(12) United States Patent
Grob et al.

(10) Patent No.: US 7,785,884 B2
(45) Date of Patent: Aug. 31, 2010

(54) LOW DENSITY SPREADING METHODS FOR CONIFER SOMATIC EMBRYOGENESIS

(75) Inventors: James A Grob, Bonney Lake, WA (US); Stephanie A Brusig, Seattle, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 0 days.

(21) Appl. No.: 11/856,570

(22) Filed: Sep. 17, 2007

(65) Prior Publication Data

US 2008/0081371 A1 Apr. 3, 2008

Related U.S. Application Data

(60) Provisional application No. 60/827,376, filed on Sep. 28, 2006.

(51) Int. Cl.
*C12N 5/00* (2006.01)
(52) U.S. Cl. .................................................. 435/422
(58) Field of Classification Search .................. 435/422
See application file for complete search history.

(56) References Cited

U.S. PATENT DOCUMENTS

| | | | |
|---|---|---|---|
| 5,413,930 A | 5/1995 | Becwar et al. | |
| 5,491,090 A | 2/1996 | Handley et al. | |
| 5,506,136 A | 4/1996 | Becwar et al. | |
| 5,548,924 A * | 8/1996 | Mekler | 47/69 |
| 6,180,405 B1 | 1/2001 | Aitken-Christie et al. | |
| 6,200,809 B1 * | 3/2001 | Klimaszewska et al. | 435/422 |
| 6,692,963 B1 | 2/2004 | Bausher et al. | |
| 6,964,870 B2 | 11/2005 | Connett-Porceddu et al. | |
| 7,157,620 B2 | 1/2007 | Connett-Porceddu et al. | |
| 2002/0092037 A1 * | 7/2002 | Connett-Porceddu et al. | 800/278 |
| 2004/0096970 A1 | 5/2004 | Gupta et al. | |
| 2004/0267457 A1 | 12/2004 | Timmis et al. | |
| 2005/0287660 A1 | 12/2005 | Aubry et al. | |
| 2006/0051868 A1 | 3/2006 | Pullman et al. | |
| 2007/0099293 A1 * | 5/2007 | Gupta et al. | 435/289.1 |
| 2007/0101463 A1 | 5/2007 | Gupta et al. | |

FOREIGN PATENT DOCUMENTS

| AU | 2004203346 | 2/2005 |
|---|---|---|
| WO | 9105854 | 5/1991 |

OTHER PUBLICATIONS

Atree et al. Production of vigorous, desiccation tolerant white spruce (*Picea glauca* [Moench.] Voss.) synthetic seeds in a bioreactor. Plant Cell Reports (1994) 13: 601-606.*
Ogita et al. Control of the development of somatic embryo of Japanes conifers by the density of embryogenic cells in liquid culture. Transplant Production in the 21*st* Century, 2000, 209-214.*
Gupta et al. Conifer somatic embryo production from liquid culture. Plant Biotechnology and In Vitro Biology in the 21*st* Century, Klewer Acad. Pub., 1999 pp. 49-52.*
Attree AM et al, "Production of vigorous, dessication tolerant while spruce (*Picea glauca* [Moench.] Voss.) synthetic seeds in a bioreactor," *Plant Cell Rep* 13: 601-606 (1994).
Etienne-Barry D et al, "Direct sowing of *Coffea arabica* somatic embryos mass-produced in a bioreactor and regeneration of plants," *Plant Cell Rep* 17: 111-117 (1999).
Garin E et al., "Effect of sugars, amino acids, and culture technique on maturation of somatic embryos of *Pinus strobus* on medium with two gellan gum concentrations," *Plant Cell, Tiss and Org Cult* 62: 27-27 (2000).
Harvengt L, "Somatic Embryogenesis in maritime pine (*Pinus pinaster* AIT.)," *Jain and Gupta, eds., Protocol for Somatic embryogenesis in Woody Plants*, 107-119, 2005 Springer pub.
Krogstrup P, "Effect of culture densities on cell proliferation and regeneration from embryonic cell suspensions of *Picea sitchensis*," *Plant Sci* 72, 115-123 (1990).
Lai FM et al, "Effect of nutrition on maturation of alfalfa (*Medicago sativa* L.) somatic embryos," *Plant Sci* 91, 87-95 (1993).
Lai FM et al, "Scale-up of somatic embryogenesis in alfalfa (*Medicago saliva* L.), I Subculture and indirect secondary somatic embryogenesis," *Plant Cell, Tiss and Org Cult* 37: 151-158 (1994).
Ramarosandratana A et al., "Influence of the embryonal-suspensor mass (ESM) sampling on development and proliferation of maritime pine somatic embryos," *Plant Sci* 160, 473-479 (2001).
Salajova T et al, "Initiation of embryogenic tissues and plantlet regenerations from somatic embryos of *Pinus nigra* Arn.," *Plant Sci* 145, 33-40 (1999).
Tremblay FM, "Protocol of somatic embryogenesis: Black spruce (*Picea mariana* (Mill.) B.S.P.," Jain and Gupta, eds., *Protocol for Somatic embryogenesis in Woody Plants*, 59-68, 2005 Springer pub.
Walter C et al., "Somatic embryogenesis and genetic transformation in *Pinus radiata*," Jain and Gupta, eds., *Protocol for Somatic embryogenesis in Woody Plants*, 11-24, 2005 Springer pub.
Boulay, M.P., et al; Development of somatic embryos from cell suspension cultures of Norway spruce (*Picea abies* Karst), Department of Environmental Horticulture, University of California, Davis CA US, Nov. 20, 1987.

* cited by examiner

*Primary Examiner*—June Hwu
(74) *Attorney, Agent, or Firm*—Christensen, O'Connor Johnson, Kindness PLLC

(57) ABSTRACT

In one aspect, the present invention provides methods of producing conifer cotyledonary somatic embryos from pre-cotyledonary embryos. The methods of this aspect of the invention include the step of (a) dispensing a plurality of pre-cotyledonary embryos onto a porous material horizontally disposed over a non-porous surface in a volume of sterile dilution medium sufficient to submerge at least the surface of the porous material, thereby uniformly dispersing the pre-cotyledonary embryos; (b) removing the sterile dilution medium from the non-absorbent porous material, thereby trapping the uniformly dispersed pre-cotyledonary embryos on the porous material; and (c) contacting the pre-cotyledonary embryos trapped on the porous material with development medium for a period of time sufficient to produce conifer cotyledonary somatic embryos.

11 Claims, 2 Drawing Sheets

LOW DENSITY SPREADING METHODS FOR CONIFER SOMATIC EMBRYOGENESIS

CROSS REFERENCE TO RELATED APPLICATION

The present application claims the benefit of U.S. Provisional Application No. 60/827,376, filed Sep. 28, 2006.

FIELD OF THE INVENTION

The present invention relates to methods for producing plant embryos in vitro, and optionally producing plants from plant embryos.

BACKGROUND OF THE INVENTION

The demand for coniferous trees, such as pines and firs, to make wood products continues to increase. One proposed solution to the problem of providing an adequate supply of coniferous trees is to identify individual coniferous trees that possess desirable characteristics, such as a rapid rate of growth, and to produce numerous, genetically identical, clones of the superior trees by somatic cloning.

Somatic cloning is the process of creating genetically identical trees from tree somatic tissue. Tree somatic tissue is tree tissue other than the male and female gametes. In one approach to somatic cloning, tree somatic tissue is cultured in an initiation medium which includes hormones, such as auxins and/or cytokinins, that initiate formation of embryogenic cells that are capable of developing into somatic embryos. The embryogenic cells are then further cultured in a maintenance medium that promotes multiplication of the embryogenic cells to form pre-cotyledonary embryos (i.e., embryos that do not possess cotyledons). The multiplied embryogenic cells are then cultured in a development medium that promotes development and maturation of cotyledonary somatic embryos which can, for example, be placed within artificial seeds and sown in the soil where they germinate to yield conifer seedlings. The seedlings can be transplanted to a growth site for subsequent growth and eventual harvesting to yield lumber, or wood-derived products. Alternatively, the cotyledonary somatic embryos can also be germinated in a germination medium, and thereafter transferred to soil for further growth.

A continuing problem with somatic cloning of conifer embryos is stimulating efficient and cost effective formation of somatic embryos that are capable of germinating to yield plants. Preferably conifer somatic embryos, formed in vitro, are physically and physiologically similar, or identical to conifer zygotic embryos formed in vivo in conifer seeds. There is, therefore a continuing need for methods for producing viable conifer somatic embryos from conifer embryogenic cells.

SUMMARY OF THE INVENTION

In one aspect the present invention provides methods of producing conifer cotyledonary somatic embryos from pre-cotyledonary embryos. The methods of this aspect of the invention include the step of (a) dispensing a plurality of pre-cotyledonary embryos onto a porous material horizontally disposed over a non-porous surface in a volume of sterile dilution medium sufficient to submerge at least the surface of the porous material, thereby uniformly dispersing the pre-cotyledonary embryos; (b) removing the sterile dilution medium from the porous material, thereby trapping the uniformly dispersed pre-cotyledonary embryos on the porous material, and (c) contacting the pre-cotyledonary embryos trapped on the porous material with development medium for a period of time sufficient to produce conifer cotyledonary somatic embryos.

In another aspect, the present invention provides methods of producing conifer cotyledonary somatic embryos from conifer somatic cells. The methods of this aspect of the invention include the steps of (a) culturing conifer somatic cells in an induction medium to yield embryogenic cells; (b) culturing the embryogenic cells prepared in step (a) in a liquid maintenance medium to form pre-cotyledonary conifer somatic embryos; (c) dispensing a plurality of pre-cotyledonary embryos prepared in step (b) onto a porous material horizontally disposed over a non-porous surface in a volume of sterile dilution medium sufficient to submerge at least the surface of the porous material, thereby uniformly dispersing the pre-cotyledonary embryos; (d) removing the sterile dilution medium from the porous material, thereby trapping the uniformly dispersed pre-cotyledonary embryos on the porous material; and (e) contacting the pre-cotyledonary embryos trapped on the porous material with development medium for a period of time sufficient to produce conifer cotyledonary somatic embryos.

The methods of the invention produce a higher yield of conifer somatic embryos than an equivalent method in which the pre-cotyledonary embryos are not uniformly dispersed over development medium. In some embodiments, the plurality of the pre-cotyledonary embryos are dispensed in sterile dilution medium at a density of less than 0.1 gram wet cell weight per square inch of porous material, such as from 0.005 to 0.1 gram wet cell weight per square inch of porous material. In some embodiments, the plurality of the pre-cotyledonary embryos are dispensed in sterile dilution medium at a density of less than 0.05 gram wet cell weight per square inch of porous material, such as from 0.001 to 0.05 gram wet cell weight per square inch of porous material.

The methods of the invention are useful, for example, for preparing conifer somatic embryos that can be used for later maturation steps and/or that can be germinated to yield conifer plants that can be grown into mature conifer trees, if so desired. Thus, for example the methods of the invention can be used to produce clones of individual conifer trees that possess one or more desirable characteristics, such as a rapid growth rate or improved wood quality. For example, a population of conifer somatic embryos produced using the methods of the invention can be used to produce a stand or forest, of conifer trees possessing one or more desirable characteristics, such as a rapid growth rate or improved wood quality. The trees, in turn, can be utilized to produce wood products.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 2A-D show the drop plating method controls for genotypes A, E, F, and B, respectively. FIGS. 2E-H show the results of the liquid dispersion confluent spread plating method for genotypes A, E, F, and B, respectively.

DETAILED DESCRIPTION OF THE PREFERRED EMBODIMENT

Figure 1:
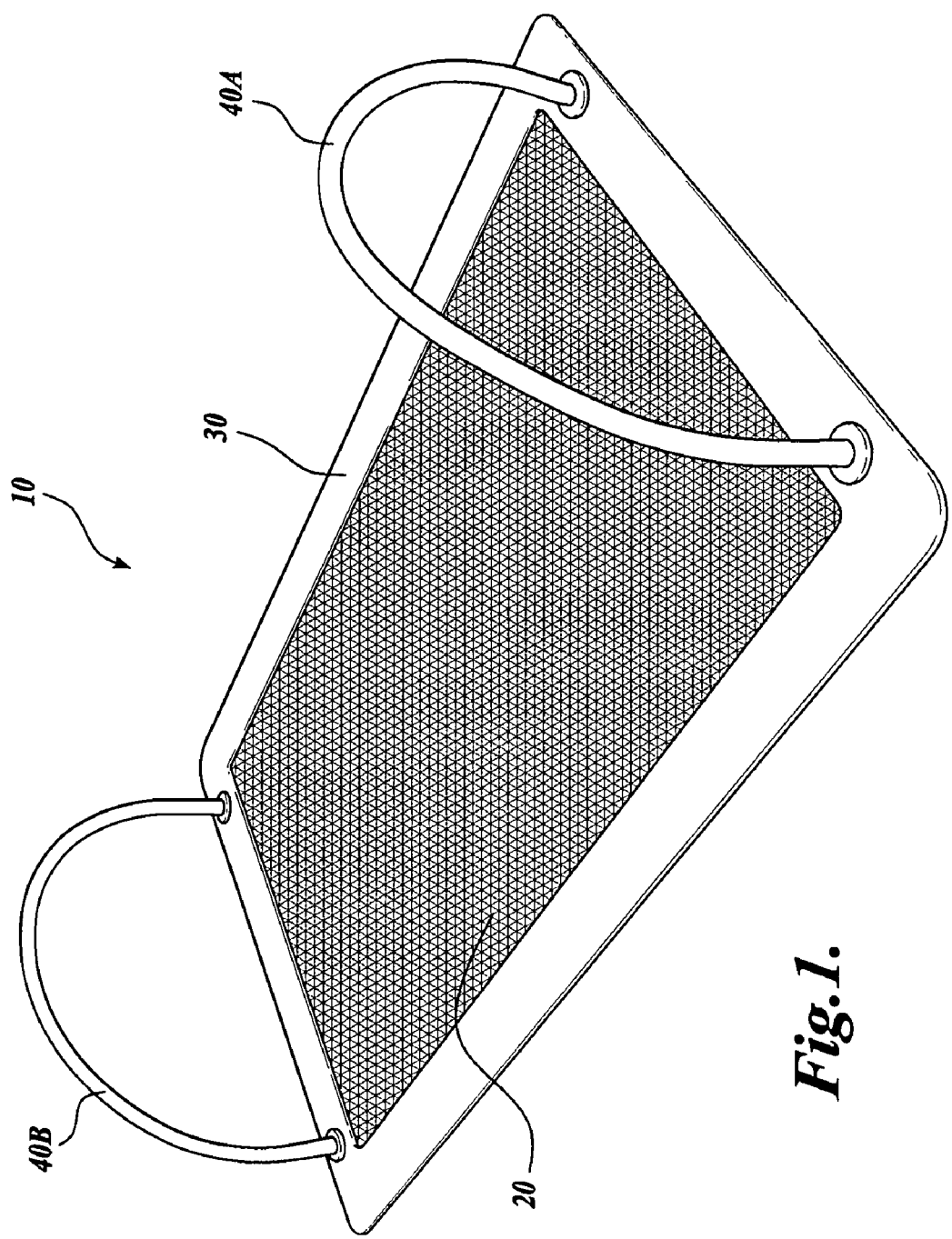
FIG. 1 illustrates an exemplary plating frame comprising porous material disposed on a support frame, for use in accordance with an embodiment of the method of the invention.

Unless specifically defined herein, all terms used herein have the same meaning as they would to one skilled in the art of the present invention.

As used herein, the term "embryogenic cells" refers to any cells, including cells that are organized to form a tissue or an organ, derived from a plant of the order Coniferales, that are capable of producing one or more conifer somatic embryos when treated in accordance with the methods of the invention. Thus, the term "embryogenic cells" includes, for example, conifer embryonal suspensor masses.

As used herein, the term "pre-cotyledonary embryo" refers to an embryo that does not yet possess any cotyledons.

As used herein, the term "cotyledonary embryo" refers to an embryo that possesses at least one cotyledon.

The present inventors have discovered that methods of the invention produce a higher yield of conifer somatic embryos than an equivalent method in which the pre-cotyledonary embryos are not uniformly dispersed over development medium. The inventors have further observed that plating pre-cotyledonary embryos according to the methods of the invention at a plating density of less than 0.1 gram wet cell weight per square inch of porous material, such as from 0.001 to 0.1 gram wet cell weight per square inch of porous material, produces an increased yield of cotyledonary embryos per unit area as compared to pre-cotyledonary embryos plated at a higher density and/or plated using a traditional pipette drop method, as further described in Examples 2 and 3.

In accordance with the foregoing, in one aspect, the present invention provides methods of producing conifer cotyledonary somatic embryos from pre-cotyledonary embryos. The methods of this aspect of the invention include the step of (a) dispensing a plurality of pre-cotyledonary embryos onto a porous material disposed horizontally over a non-porous surface in a volume of sterile dilution medium sufficient to submerge at least the surface of the porous material, thereby uniformly dispersing the pre-cotyledonary embryos; (b) removing, the sterile dilution medium from the porous material, thereby trapping the uniformly dispersed pre-cotyledonary embryos on the porous material; and (c) contacting the pre-cotyledonary embryos trapped on the porous material with development medium for a period of time sufficient to produce conifer cotyledonary somatic embryos.

The methods of the invention can be used to produce cotyledonary somatic embryos from any conifer, such as members of the genus *Pinus*, such as Loblolly Pine (*Pinus taeda*) and Radiata pine. Again, by way of example, Douglas-fir cotyledonary somatic embryos can be produced by the methods of the invention.

In accordance with the methods of the invention, a plurality of pre-cotyledonary conifer somatic embryos to be plated are suspended into a volume of sterile dilution medium sufficient to submerge at least the surface of the porous material disposed on the non-porous substrate. The plurality of pre-cotyledonary embryos may be generated using the methods described herein. For example, suspension cultures of immature somatic embryos (pre-cotyledonary embryos) may be cultured in a liquid maintenance medium and the cells allowed to settle. The settled cell volume (SCV) is then measured, using any suitable method, such as the method described in Example 2. The desired amount of SCV is then diluted with the sterile dilution media for plating at a desired density. In some embodiments, the amount of dilution medium used to dilute the SCV is chosen based on the surface area of the plating frame, in order to be sufficient to submerge at least the surface of the porous material attached to the frame. For example, the SCV may be diluted with an amount of sterile dilution media at least about 3 to 4 times or more of the SCV volume.

The sterile dilution medium may be any suitable liquid medium that maintains the ability of the embryos to survive and maintain their developmental status, such as, for example maintenance media or the exemplary dilution media shown below in TABLE 2.

In some embodiments of the method, the pre-cotyledonary embryos are plated at a low density, such as less than about 0.1 grain wet cell weight per square inch of porous material plating area, assuming an average wet weight of about 0.1 g/ml SCV. The average wet weight of SCV may be determined as described in Example 2. For example, the embryos may be plated at less than 0.05 gram, or less than 0.025 grams wet cell weight per square inch of porous material plating area. In some embodiments, the pre-cotyledonary embryos are plated at a low density in a range from about 0.001 gram to about 0.1 gram wet cell weight per square inch of porous material plating area (e.g., from 1 ml SCV to 0.01 ml SCV per square inch of porous material plating area). Iii one embodiment, the pre-cotyledonary embryos are plated at a density in a range from about 0.01 grams to about 0.08 grams wet cell weight per square inch of porous material plating area, such as from about 0.02 grams to about 0.05 grams wet cell weight per square inch of porous material plating area.

Porous materials that are useful in the practice of the present invention have a pore diameter in the range of from about 5 microns to about 1200 microns, such as from about 50 microns to about 500 microns, such as from about 70 to about 150 microns, such as about 100 microns. The porous material is typically planar and may be any desired shape and dimension. The shape and dimension of the porous material are chosen for ease of manipulation and for placement onto a growth substrate such as development media. Suitable shapes include square, rectangular or circular shapes. Exemplary dimension are from a surface area of about 14 square inches to 28 square inches or greater, such as 50 square inches, 100 square inches up to 500 square inches or greater. Preferred porous materials are sterilizable and sufficiently strong to resist tearing when the materials are lifted in order to transfer somatic embryos after plating to subsequent stages of the somatic embryo production process. Examples of useful porous materials include membranes, nylon fiber, woven mesh (e.g., nylon, stainless steel or plastic) and polymeric fibers. In some embodiments, the porous material is non-absorbent. In some embodiments, the porous material is a woven mesh, such as a stainless steel or nylon mesh.

In accordance with an embodiment of the method of the invention, a porous material, such as for example, a woven mesh, is used to plate and support plant tissue during the development phase of plant somatic embryo production. The pre-cotyledonary somatic embryos are initially dispensed onto a planar porous material which is disposed horizontally over a non-porous surface. The non-porous surface may be any suitable sterile surface, such as, for example, the surface of a solid or semi-solid growth medium, such as a petri dish containing development medium, or any other sterile or sterilizable surface capable of retaining liquid, such as a plastic, rubber, or glass surface. In some embodiments, the non-porous surface is semi-solid development medium contained in a box, such as a cambro box. In some embodiments, the non-porous surface is contained within a bioreactor vessel, wherein the bioreactor vessel is drainable.

In one embodiment of the method, the porous material is attached to a plating frame. A representative example of a plating frame 10 is shown in FIG. 1. As shown in FIG. 1, the plating frame 10 comprises a planar porous material 20 attached to a support frame 30 that surrounds the porous material 20. Optional handles 40A, 40B are provided that are attached to the support frame 30. The plating frame is preferably made of materials that are sterilizable. For example, the support frame 30 may be made of a metal or plastic material. The handles 40A, 40B may be made of any suitable sterilizable material, such as, for example, autoclavable tubing. An exemplary method for constructing the plating frame 10 is described in Example 2. In one embodiment, the support frame 30 is metal and the porous material is a nylon mesh which is attached to the frame prior to autoclaving and moderately shrinks after autoclaving to produce a taut attachment to the frame and a substantially level plating surface.

In accordance with the methods of the invention a plurality of pre-cotyledonary embryos are dispensed onto a porous material disposed over a non-porous surface in a volume of sterile dilution medium sufficient to submerge at least the surface of the porous material. The pre-cotyledonary embryos are thereby uniformly dispersed across the submerged surface of the porous material. In some embodiments, the dispensed embryos are gently mixed or agitated to facilitate dispersion of the embryos in the sterile dilution medium. Gentle agitation may be achieved by any suitable means, such as, for example, via the use of an instrument contacting the embryos, or via vibration of the porous material and/or the non-porous substrate.

Once the dispensed pre-cotyledonary embryos are substantially uniformly dispersed over the porous material, the sterile dilution medium is removed from the porous material. In one embodiment, the sterile dilution medium is removed from the porous material by vertically lifting the porous material off the non-porous substrate, thereby trapping the uniformly dispersed pre-cotyledonary embryos on the surface of the porous material. For example, the porous material attached to a plating frame 10 comprising handles 40A, 40B, may be vertically lifted by the handles using any suitable means, such as manually or through robotic means.

In an alternative embodiment, once the dispensed pre-cotyledonary embryos are substantially uniformly dispersed over the porous material, the sterile dilution medium is removed by reducing the volume of the sterile dilution medium to a level below the surface of the porous material, thereby trapping the uniformly dispersed pre-cotyledonary embryos on the surface of the porous material. The volume of sterile dilution medium may be reduced using any method that avoids disturbing the distribution of plated cells, such as, for example, suctioning, draining, tipping, or blotting off the sterile dilution medium.

The uniformly dispersed pre-cotyledonary embryos trapped on the surface of the porous material are then contacted with development medium for a period of time sufficient to produce conifer cotyledonary somatic embryos.

In one embodiment, the porous material is either continuously or intermittently contacted with liquid development medium. For example, the porous material may be placed on an absorbent pad which is soaked in development medium so that the development medium passes through the porous material and contacts the embryos. The porous material, such as a nylon mesh bearing embryonic cells, is typically enclosed within a sealed space which contains a humid atmosphere that ensures that the embryos remain moist. In another embodiment, the porous material is disposed on a growth substrate comprising solid or semi-solid development media.

The development medium for use in the methods of the invention contains nutrients that sustain the somatic embryos. Maltose and glucose may be included in the development medium as the principal or sole source of sugar for the somatic embryos. Useful maltose and glucose concentrations are within the range of from about 1% to about 2.5%. Suitable development media typically do not include growth-promoting hormones, such as auxins and cytokinins, but may include the hormone abscisic acid. When abscisic acid is utilized in the development medium, it is typically utilized at a concentration in the range of from about 1 mg/L to about 200 mg/L. The development medium may contain gellan gum, typically present at a concentration of up to about 0.40%. The osmolality of the development medium can be adjusted to a value that falls within a desired range, using osmoticants such as PEG 8000 molecular weight, such as from about 250 mM/Kg to about 450 mM/Kg. Typically, an osmolality of 300-350 mM or higher is advantageous. An example of suitable liquid or solid development medium is provided in Example 1 and Example 2.

By way of example, pre-cotyledonary conifer somatic embryos may be cultured on a porous material, such as a nylon mesh or membrane that is at least intermittently contacted with development medium, for a period of from 4 weeks to 14 weeks, such as from 8 weeks to 12 weeks, or such as about 12 weeks, at a temperature of from 10° C. to 30° C., such as from 15° C. to 25° C., or such as from 20° C. to 23° C.

In one embodiment, the pre-cotyledonary conifer somatic embryos are cultured on a porous material contacted with liquid development media that is applied to an absorbent substrate, such as a substrate made from cellulose (e.g., cellulose fibers), such as one or more filter papers, or some other absorbent material. The substrate absorbs the liquid development medium which passes through the porous material disposed on the substrate and contacts conifer precotyledonary somatic embryos disposed on the porous material. The development medium promotes the development of the conifer precotyledonary somatic embryos to form cotyledonary somatic embryos.

In another embodiment, the pre-cotyledonary conifer somatic embryos are cultured on a porous material contacted with liquid development medium using an atomiser which sprays the porous material with development medium. The somatic embryos are disposed on an upper surface of the porous material and the opposite, lower surface of the porous material is sprayed with liquid development medium. By way of further example, the porous material bearing somatic embryos can be disposed over liquid development medium that includes a rotating stir bar which rotates sufficiently fast to spray liquid development medium up onto the lower surface of the porous material.

In another aspect, the present invention provides methods of producing conifer cotyledonary somatic embryos from conifer somatic cells. The methods of this aspect of the invention include the step of (a) culturing conifer somatic cells in an induction medium to yield embryogenic cells; (b) culturing the embryogenic cells prepared in step (a) in a liquid maintenance medium to form pre-cotyledonary conifer somatic embryos; (c) dispensing a plurality of pre-cotyledonary embryos prepared in step (b) onto a porous material disposed over a non-porous surface in a volume of sterile dilution medium sufficient to submerge at least the surface of the porous material, thereby uniformly dispersing the pre-cotyledonary embryos; (d) removing the sterile dilution medium from the porous material, thereby trapping the uniformly dispersed pre-cotyledonary embryos on the porous material; and (e) contacting the pre-cotyledonary embryos trapped on the porous material with development medium for a period of time sufficient to produce conifer cotyledonary somatic embryos.

Thus, in some embodiments, conifer somatic cells are cultured in, or on, an induction medium to yield embryogenic cells. Embryogenic cells are capable of producing one or more cotyledonary conifer somatic embryos. Examples of embryogenic cells are embryonal suspensor masses (ESMs).

The induction medium typically includes inorganic salts and organic nutrient materials. The osmolality of the induction medium is typically about 160 mM/kg or even lower, but it may be as high as 170 mM/kg. The induction medium typically includes growth hormones. Examples of hormones that can be included in the induction medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 10 mg/L.

The induction medium may contain an adsorbent composition, especially when very high levels of growth hormones are used. The adsorbent composition can be any composition that is not toxic to the embryogenic cells at the concentrations utilized in the practice of the present methods, and that is capable of adsorbing growth-promoting hormones, and toxic compounds produced by the plant cells during embryo development, that are present in the medium. Non-limiting examples of useful adsorbent compositions include activated charcoal, soluble poly(vinyl pyrrolidone), insoluble poly(vinyl pyrrolidone), activated alumina, and silica gel. The adsorbent composition may be present in an amount, for example, of from about 0.1 g/L to about 5 g/L. The induction medium is typically solid, and may be solidified by inclusion of a gelling agent. An example of an induction medium useful in the practice of the present invention is set forth in Example 1.

Conifer somatic cells are typically cultured in, or on, an induction medium for a period of from 3 weeks to 12 weeks, such as from 8 weeks to 10 weeks, or such as about 8 weeks, at a temperature of from 10° C. to 30° C., such as from 15° C. to 25° C., or such as from 20° C. to 23° C.

The maintenance medium may be a solid medium, or it may be a liquid medium which can be agitated to promote growth and multiplication of the embryogenic tissue. The osmolality of the maintenance medium is typically higher than the osmolality of the induction medium, typically in the range of 180-400 mM/kg. The maintenance medium may contain nutrients that sustain the embryogenic tissue, and may include hormones, such as one or more auxins and/or cytokinins, that promote cell division and growth of the embryogenic tissue. Typically, the concentrations of hormones in the maintenance medium is lower than their concentration in the induction medium.

It is generally desirable, though not essential, to include maltose as the sole, or principal, metabolizable sugar source in the maintenance medium Examples of useful maltose concentrations are within the range of from about 1% to about 2.5%. An example of a suitable maintenance medium is set forth in Example 1 herein.

Conifer embryogenic cells are typically cultured in, or on, a maintenance medium for a period of up to 6 months by weekly subculture, at a temperature of from 10° C. to 30° C., such as from 15° C. to 25° C., or such as from 20° C. to 23° C.

Conifer embryogenic cells are typically transferred to fresh maintenance medium once per week or as growth exhausts media components.

Useful development media are described supra. After being cultured in continuous, or periodic, contact with a development medium, the cotyledonary somatic embryos can optionally be transferred to a maturation medium, and then to a stratification medium, for a further period of culture.

The methods of the invention can be used, for example, to produce clones of individual conifer trees that possess one or more desirable characteristics, such as a rapid growth rate. Thus, in one aspect, the present invention provides methods for producing a population of genetically-identical, conifer, cotyledonary, somatic embryos. The methods of this aspect of the invention each include the step of culturing genetically-identical, conifer, precotyledonary somatic embryos on a porous material (e.g., porous nylon mesh) that is in continuous, or periodic, contact with a development medium, for a period of time sufficient to produce genetically-identical, conifer, cotyledonary, somatic embryos from the precotyledonary somatic embryos, wherein the development medium passes through the porous material and contacts the somatic embryos.

The conifer cotyledonary somatic embryos produced using the methods of the invention can optionally be germinated to form conifer plants which can be grown into coniferous trees, if desired. The cotyledonary embryos may also be disposed within artificial seeds for subsequent germination. The conifer cotyledonary somatic embryos can be germinated, for example, on a solid germination medium, such as the germination medium described in Example 2 herein. The germinated plants can be transferred to soil for further growth. For example, the germinated plants can be planted in soil in a greenhouse and allowed to grow before being transplanted to an outdoor site. Typically, the conifer cotyledonary somatic embryos are illuminated to stimulate germination. Typically, all the steps of the methods of the invention, except germination, are conducted in the dark.

The methods of the invention produce a higher yield of conifer somatic embryos per surface area plated than an equivalent method in which the embryogenic cells are plated at a higher density and/or in the presence of excess liquid, as further described in Examples 2 and 3 supra.

The methods of the invention can be used, for example, to produce clones of individual conifer trees that possess one or more desirable characteristics, such as a rapid growth rate. The methods described herein can be used to produce populations of genetically-identical, mature somatic conifer embryos.

The following examples merely illustrate the best mode now contemplated for practicing the invention, but should not be construed to limit the invention.

EXAMPLE 1

This Example shows a representative method of the invention for producing somatic pine embryos from Loblolly Pine.

Female gametophytes containing zygotic embryos are removed from seeds four to five weeks after fertilization. The seed coats are removed but the embryos are not further dissected out of the surrounding gametophyte other than to excise the nucellar end. The cones were stored at 4° C. until used. Immediately before removal of the immature embryos, the seeds are sterilized utilizing an initial washing and detergent treatment followed by a ten minute sterilization in 15% $H_2O_2$. The explants were thoroughly washed with sterile distilled water after each treatment.

Tables 1 and 2 set forth exemplary compositions of media useful for producing pine somatic embryos.

TABLE 1

Pinus Taeda Basal Medium (BM)

| Constituent | Concentration (mg/L) |
|---|---|
| $NH_4NO_3$ | 150.0 |
| $KNO_3$ | 909.9 |
| $KH_2PO_4$ | 136.1 |
| $Ca(NO_3)_2 \cdot 4H_2O$ | 236.2 |
| $CaCl_2 \cdot 4H_2O$ | 50.0 |
| $MgSO_4 \cdot 7H_2O$ | 246.5 |
| $Mg(NO_3)_2 \cdot 6H_2O$ | 256.5 |
| $MgCl_2 \cdot 6H_2O$ | 50.0 |
| KI | 4.15 |
| $H_3BO_3$ | 15.5 |
| $MnSO_4 \cdot H_2O$ | 10.5 |
| $ZnSO_4 \cdot 7H_2O$ | 14.4 |
| $NaMoO_4 \cdot 2H_2O$ | 0.125 |
| $CuSO_4 \cdot 5H_2O$ | 0.125 |
| $CoCl_2 \cdot 6H_2O$ | 0.125 |
| $FeSO_4 \cdot 7H_2O$ | 27.86 |
| $Na_2EDTA$ | 37.36 |
| Maltose | 30,000 |
| myo-Inositol | 200 |
| Casamino acids | 500 |
| L-Glutamine | 1000 |
| Thiamine-HCl | 1.00 |
| Pyridoxine-HCl | 0.50 |
| Nicotinic acid | 0.50 |
| Glycine | 2.00 |
| Gelrite+ | 1600 |
| pH adjusted to 5.7 | |

+Used if a solid medium is desired.

TABLE 2

Composition of Media for Different Stage Treatments

| | |
|---|---|
| $BM_1$ - Induction Medium | BM + 2,4-D (15 µM) + Kinetin (2 µM) + BAP (2 µM). |
| $BM_2$ - Maintenance Medium | BM + 2,4-D (5 µM) + Kinetin (0.5 µM) + BAP (0.5 µM). GELRITE (1600 mg/L) is added when a solid medium is desired. |
| Dilution Medium | BM + 10 mg/mL abscisic acid + 100-1000 mg/mL additional myo-inositol, +2.5% Maltose. The following amino acid mixture is added: L-proline (100 mg/L), L-asparagine (100 mg/L), L-arginine (50 mg/L), L-alanine (20 mg/L), and L-serine (20 mg/L). Preferably no maintenance hormones are present. |
| $BM_3$ - Development Medium | BM + 25 mg/L abscisic acid + 12% PEG-8000 + 800 mg/L additional myo-inositol + 0.1% activated charcoal + 1% glucose, +2.5% Maltose. The following amino acid mixture is added: L-proline (100 mg/L), L-asparagine (100 mg/L), L-arginine (50 mg/L), L-alanine (20 mg/L), and L-serine (20 mg/L). GELRITE (2500 mg/L) is added when a solid medium is desired. |
| $BM_5$ - Stratification Medium | $BM_3$ modified by omitting abscisic acid, and PEG-8000. GELRITE (2500 mg/L) is added when a solid medium is desired. |
| $BM_6$ - Germination Medium | BM modified by replacing maltose with 2% sucrose. Myo-inositol is reduced to 100.0 mg/L, glutamine and casamino acids are reduced to 0.0 mg/L. $FeSO_4 \cdot 7H_2O$ is reduced to 13.9 mg/L and $Na_2EDTA$ reduced to 18.6 mg/L. Agar at 0.8% and activated charcoal at 0.25% are added. |

Induction: Sterile gametophytes with intact embryos are placed on a solid $BM_1$ culture medium and held in an environment at 22°-25° C. with a 24 hour dark photoperiod for a time of 3-5 weeks. The length of time depends on the particular genotype being cultured. At the end of this time, a white mucilaginous mass forms in association with the original explants. Microscopic examination typically reveals numerous early stage embryos associated with the mass. These are generally characterized as having a long thin-walled suspensor associated with a small head with dense cytoplasm and large nuclei.

Osmolality of the induction medium may in some instances be as high as 150 mM/kg. Normally it is about 120 mM/kg or even lower (such as 110 mM/kg).

Maintenance and Multiplication of Pre-cotyledonary Embryos: Early stage embryos removed from the masses generated in the induction stage are first placed on a $BM_2$ gelled maintenance and multiplication medium. This differs from the induction medium in that the growth hormones (both auxins and cytokinins) are reduced by at least a full order of magnitude. Osmolality of this medium is at 130 mM/kg or higher (typically within the range of about 120-150 mM/kg for Pinus taeda). The temperature is again 22°-25° C. in the dark. Embryos are cultured 12-14 days on the $BM_2$ solid medium before transferring to a liquid medium for further subculturing. This liquid medium has the same composition as $BM_2$, but lacks the gellant. The embryos at the end of the solid maintenance stage are typically similar in appearance to those from the induction stage. After 5 to 6 weekly subcultures on the liquid maintenance medium, advanced early stage embryos have formed. These are characterized by smooth embryonal heads, estimated to typically have over 100 individual cells, with multiple suspensors.

Embryo Development: Embryo development is conducted as described below in Examples 2 and 3.

The osmotic potential of this development medium may be raised substantially over that of the maintenance medium. It has been found advantageous to have an osmolality as high as 300 mM/kg or even higher. Development is preferably carried out in complete darkness at a temperature of 22°-25° C. until cotyledonary embryos have developed. Development time is typically several weeks, such as 7 to 12 weeks.

Stratification: Cotyledonary embryos are singulated and transferred to stratification medium $BM_5$. This medium is similar to development medium but lacks abscisic acid, PEG-8000, and gellan gum. Embryos are cultivated on stratification medium at between about 1° C. and about 10° C. in the dark for between three to six weeks.

Conditioning over water: The mature embryos still on the porous material are lifted from the growth substrate and placed in a closed container over $H_2O$ at a relative humidity of 97%, for a period of about three weeks.

Germination: The conditioned mature embryos were placed on solid $BM_6$ medium for germination. This is a basal medium lacking growth hormones which has been modified by reducing sucrose, myo-inositol and organic nitrogen. The embryos are incubated on $BM_6$ medium for sufficient time under environmental conditions of 23°-25° C. until the resulting plantlets have a well developed radicle and hypocotyl and green cotyledonary structure and epicotyl.

Because of the reduced carbohydrate concentration, the osmotic potential of the germination medium is further reduced below that of the development medium. It is normally below about 150 mM/kg (such as about 100 mM/kg).

EXAMPLE 2

This example describes the construction an exemplary plating frame and use according to an embodiment of the method of the invention.

Construction of a Plating Frame: A metal plating frame was constructed to which a 100 micron nylon weave mesh was attached by silicone. The plating frame (10) is shown in FIG. 1. In the embodiment of the plating frame (10) shown in FIG. 1, the nylon weave mesh (20) is rectangular in shape, with a length of 7 inches and a width of 4 inches, having an exposed surface area of 28 square inches. Tubing handles (40A, 40B) were attached to the metal frame (30) to facilitate movement of the plating frame (10). A silicon bead was added along the edge of the frame and across the middle of the frame to create 2 separated plating areas of equal size (not shown). The plating frame (10) was then autoclaved, resulting in a taut plating surface due to shrinkage of the nylon weave mesh (20) onto the metal frame (30) during autoclaving.

Planting Cells on the Plating Frame:

Preparation of the SCV for plating: Conifer somatic embryo cells of genotype A that were grown in proliferation medium (made as described in TABLE 4) in 1 liter Ehrlemeyer flasks were allowed to settle. The settled cell volume (SCV) was measured by drawing a line on the flask, and supernatant above the settled cells was withdrawn via a fritted glass wand under aspiration. The settled cells were then resuspended in a 3×SCV supplemental amount of sterile dilution medium, made as described in Example 1.

Determination of the wet weight of SCV: In order to determine wet weight of SCV, SCV was measured as described above. The supernatant was then removed using a Buchnar funnel (13 inches Hg) and 1 ml of the SCV sample was placed onto a pre-weighed, pre-moistened VWR grade 417 filter paper. Weight measurements were taken at a fixed time (30 seconds) on a 4-point balance. Wet weight measurements of four representative genotypes per ml of SCV are shown below in TABLE 3.

TABLE 3

| Genotype | wet weight mg/ml SCV |
|---|---|
| A | 92 mg/ml |
| B | 102 mg/ml |
| C | 102 mg/ml |
| D | 118 mg/ml |

From the results shown in TABLE 3, the average wet weight across 4 genotypes tested: 103.5 mg/ml SCV. Therefore, the average wet weight of 1 ml of SCV from the four genotypes tested is about 0.1 g/mL SCV.

A plating frame (10), made as described above, was provided and placed onto the surface of semi-solid development media (made as described in TABLE 5). The volume of the rinsed, settled cells was then measured, and plated onto the first half of the plating frame at a density of 3 mls SCV (0.3 g/14 square inches=0.02 g/square inch), and onto the second half of the plating frame at a density of 12 mls SCV (1.2 g/14 square inches=0.08 g/square inch), each in a total volume of 9 mls and 36 mls, respectively.

Plating of the cells was done over the plating frame placed onto the surface of a semi-solid development media contained in a box. This allowed cells and media to disperse evenly across the nylon mesh in order to minimize variation in cell density and initial cell depth. Once the plated cells were evenly dispersed over the submerged nylon mesh, the plating frame (10) was lifted vertically off the semi-solid development media, thereby capturing the evenly dispersed embryos and allowing the excess media to disperse while remaining in the first box. The plating frame containing the evenly dispersed embryos was then placed onto the surface of a semi-solid development media of the same formulation as the first in a new box. The plated cells on the plating frame were then allowed to grow for 12 weeks and monitored for total biomass, embryo suspensor mass, and embryo structure formation, as shown below in TABLE 6.

TABLE 4

Proliferation/Maintenance Medium
(Loblolly Pine)

| Constituent | Concentration (mg/L) |
|---|---|
| $NH_4NO_3$ | 150.0 |
| $KNO_3$ | 909.9 |
| $KH_2PO_4$ | 136.0 |
| $Ca(NO_3)_2 \cdot 4H_2O$ | 236.15 |
| $CaCl_2 \cdot 2H_2O$ | 50.0 |
| $MgSO_4 \cdot 7H_2O$ | 246.5 |
| $Mg(NO_3)_2 \cdot 6H_2O$ | 256.5 |
| $MgCl_2 \cdot 6H_2O$ | 50.0 |
| KI | 4.15 |
| $H_3BO_3$ | 15.5 |
| $MnSO_4 \cdot H_2O$ | 10.5 |
| $ZnSO_4 \cdot 7H_2O$ | 14.4 |
| $Na_2MoO_4 \cdot 2H_2O$ | 0.125 |
| $CuSO_4 \cdot 5H_2O$ | 0.125 |
| $CoCl_2 \cdot 6H_2O$ | 0.125 |
| $FeSO_4 \cdot 7H_2O$ | 27.86 |
| $Na_2EDTA \cdot 2H_2O$ | 37.36 |
| Maltose | 30,000 |
| Myo-Inositol | 200 |
| Casamino acids | 500 |
| L-Glutamine | 1000 |
| Thiamine-HCl | 1.00 |
| Pyridoxine-HCl | 0.50 |
| Nicotinic acid | 0.50 |
| Glycine | 2.00 |
| *Gelrite+ | 1600* |
| 2,4 D (10 mg/mL) | 1.1 mg/mL |
| 6-BAP (10 mg/mL) | 0.1 mg/mL |
| Kinetin (10 mg/mL) | 0.1 mg/mL |
| *ABA (2 mg/mL) | 1.0 mg/L* |
| pH adjusted to 5.7 | (* = optional) |

TABLE 5

Development Medium (Loblolly Pine)

| Constituent | Concentration (mg/L) |
|---|---|
| NH$_4$NO$_3$ | 150.0 |
| KNO$_3$ | 909.9 |
| KH$_2$PO$_4$ | 136.0 |
| Ca(NO$_3$)$_2$•4H$_2$O | 236.15 |
| CaCl$_2$•2H$_2$O | 50.0 |
| MgSO$_4$•7H$_2$O | 246.5 |
| Mg(NO$_3$)$_2$•6H$_2$O | 256.5 |
| MgCl$_2$•6H$_2$O | 50.0 |
| KI | 4.15 |
| H$_3$BO$_3$ | 15.5 |
| MnSO$_4$•H$_2$O | 10.5 |
| ZnSO$_4$•7H$_2$O | 14.4 |
| Na$_2$MoO$_4$•2H$_2$O | 0.125 |
| CuSO$_4$•5H$_2$O | 0.125 |
| CoCl$_2$•6H$_2$O | 0.125 |
| FeSO$_4$•7H$_2$O | 27.86 |
| Na$_2$EDTA•2H$_2$O | 37.36 |
| Maltose | 25,000 |
| Glucose | 10,000 |
| Myo-Inositol | 100-2000 |
| Casamino acids | 500 |
| L-Glutamine | 1000 |
| Thiamine•HCl | 1.00 |
| Pyridoxine•HCl | 0.50 |
| Nicotinic acid | 0.50 |
| Glycine | 2.00 |
| Proline | 100 |
| L-Arginine | 50 |
| L-Asparagine | 100 |
| L-Alanine | 20 |
| L-Serine | 20 |
| PEG | 100000 |
| Charcoal | 1000 |
| Gelrite+ | 2500 |
| ABA (2 mg/mL) | 25.0 mg/L |
| pH adjusted to 5.7 | |

Results:

The cultures plated at different densities within the plating frame were examined after 12 weeks in culture for total biomass, embryo suspensor mass (ESM), and embryo structure formation. Select embryos refers to the presence of at least 4 cotyledons and no large scale deformities. The results are shown below in TABLE 6.

TABLE 6

| Plating Density | Final Wet Biomass (g) | Total Dry Biomass (mg) | Dry ESM (mg) | Dry Embryo (mg) | Number of Select Embryos |
|---|---|---|---|---|---|
| Low Density (half frame) 3 ml SCV plated | 17.0 g total (5.67 g/ml SCV plated) | 1277.6 mg total (425.87 mg/ml SCV plated) | 235 mg total (78.33 mg/ml SCV plated) | 291.8 mg total (97.27 mg/ml SCV plated) | 720 total (240 per ml SCV plated) |
| High Density (half frame) 12 ml SCV plated | 14.0 g total (1.17 g/ml SCV plated) | 1302.4 mg total (108.53 mg/ml SCV plated) | 138.7 mg total (11.56 mg/ml SCV plated) | 312.0 mg total (26.0 mg/ml SCV plated) | 771 total (64.25 per ml SCV plated) |

As shown above in TABLE 6, when the embryos were plated at a lower density (e.g., 3 ml SCV/14 square inches (approx 0.3 g/14 square inches=0.02 g/square inch)), the subsequent proliferation of the embryo suspensor masses yielded as much total biomass as the cells plated at a higher density of 12 mls SCV/14 square inches (approx. 1.2 g/14 square inches=0.08 g/square inch). As further shown in TABLE 6, the total amount of embryos produced on a per area basis was nearly equal between the low density and high density. This was made possible by the greatly enhanced embryo suspensor mass (ESM) growth as shown by the difference in dry weight, e.g., 235 mg dry ESM from the low density, versus only 138.7 mg dry ESM from the high density plated frame. Therefore, the select embryo formation (the end product of interest) per ml of SCV plated was clearly better in the low density plating (240 embryos/ml SCV) as compared to the high density plating (64.25 embryos/ml SCV).

EXAMPLE 3

This Example describes a comparison between embryo yields using a standard pipette drop plating method and the liquid dispersion confluent spread plating method according to an embodiment of the present invention using four different genotypes of Loblolly Pine.

Methods: An experiment was carried out to directly compare methods of plating cells onto plating frames (10) using the same amount of biomass of four different genotypes of Loblolly Pine, A, B, E, and F, while varying the plating density of the plated SCV. The yield of embryos and germination outcomes were measured.

Embryonic somatic (ESM) cells from Genotypes A, B, E and F were grown in proliferation medium (made as described in Example 2) in 1 liter Erlenmeyer flasks. The ESM cells were allowed to settle and the settled cell volume (SCV) was measured as described in Example 2.

For each genotype, as a control representing the standard drop plating method, 6 ml of SCV was directly plated as 12 drops (0.5 ml SCV each) onto an entire plating frame (7"×4" total area=28 square inches) placed on semi-solid development media in a shallow plating box. In this Example, a cambro box (Cambro Manufacturing Co., Huntington Beach, Calif.) that holds two plating frames (10) was utilized. To test the spread plating method, a second aliquot of 6 ml SCV from each genotype was rinsed with 3× (18 ml) of development media. The 24 ml of SCV plus rinse media was then plated onto an entire plating frame (28 square inches) disposed over a first semi-solid development media in a cambro box, such that the ESM cells floated in the media and dispersed uniformly over the submerged surface of the plating frame. The uniform dispersal was aided by gentle agitation of the plating frame. The plating frames were then lifted vertically off the first semi-solid media in the cambro box using the attached handles while maintaining the plating surface in a horizontal orientation, thereby trapping the uniformly dispersed ESM cells while allowing the media to flow through the porous mesh.

The plating frames containing plated cells were then moved to a fresh cambro box containing semi-solid development media (described in Example 2) and allowed to develop for 12 weeks. At the end of 12 weeks, the embryos were put through late development treatments to induce germination, counted, and a sample was germinated. A normal germinant was scored as having the presence of a 1 mm white root, the presence of approximately 5 epicotyl leaves approximately 5 mm long, no large scale hypocotyl ruptures, and a hypocotyl not having a bend greater than 90 degrees.

Figure 2:
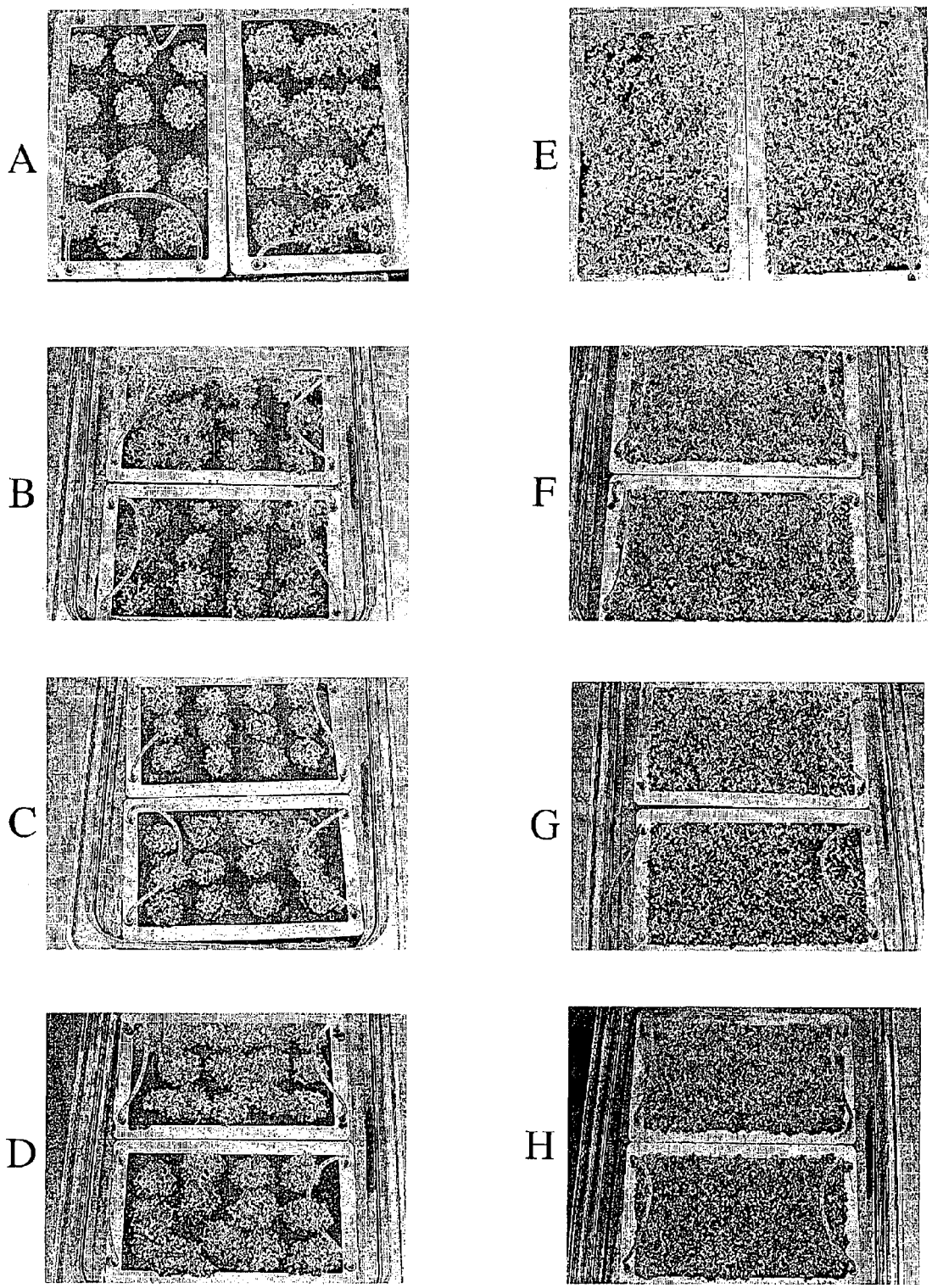
FIGS. 2A-H provides photographic images demonstrating that the growth of cotyledonary embryos plated according to the methods of the invention is improved in comparison to a standard plating method, as described in Example 3.

The total yield of developed embryos was counted after the 12 week development period. The results are shown below in TABLE 7. Photographs were taken at the end of the development period, as shown in FIG. 2. FIGS. 2A-D show the controls for genotypes A, E, F, and B, respectively. FIGS. 2E-H show the results of the liquid dispersion confluent spread plating method for genotypes A, E, F, and B, respectively.

At the end of 12 weeks, the embryos were stratified using BM5 stratification media (described in Example 1) for 4 weeks. After 4 weeks of stratification, the embryos were spray separated and conditioned over water for 10 days.

For each genotype, 25 embryos were selected for germination assessment. The embryos were selected for germination based on the presence of at least 4 cotyledons and the absence of gross deformities or split hypocotyls.

Results:

TABLE 7

| Genotype | Drop Method Embryo Yield per box (Germination %) | Spread Method Embryo Yield per box (Germination %) | Fold Increase in Embryo Yield using Spread Method |
| --- | --- | --- | --- |
| A | 2241 (52%) | 5416 (49%) | 2.4 |
| E | 2267 (15%) | 3187 (27%) | 1.4 |
| F | 1803 (8%) | 2545 (3%) | 1.4 |
| B | 2356 (10%) | 3188 (19%) | 1.3 |

As shown above in TABLE 7, all four genotypes tested showed at least a 1.3 fold or greater increase in embryo yield using the low density confluent spreading method as compared to the traditional pipette drop plating method. The results of the germination studies showed no statistically significant difference between successful germination of samples plated using the drop method versus the spreading method.

When the results of the four genotypes shown in TABLE 7 are combined, the overall mean control value of embryos produced is 2166.7 using the drop method versus the overall mean value of 3692 embryos produced using the liquid dispersion confluent spreading method, which is a 1.7 fold higher embryo yield, with a p value of 0.0708. This is a very significant improvement in embryo yields which allows a genotype to be plated in a single cambro unit to achieve the mean yield target for germination yields, and decreases the number of units required to handle a single clone down to only one in contrast to the at least 30 separate units (petri plates) required using the traditional pipette drop plating method.

The combined results recorded across the four genotypes tested are provided below in TABLE 8.

TABLE 8

| Parameter | Control Drop Plating (6 ml SCV in .5 ml drops × 12) | Spread Plating (6 ml SCV diluted in 18 ml) | p-value |
| --- | --- | --- | --- |
| Total embryo yield per box | 2167 | 3692 | 0.0708 |
| Mean embryo yield per ml SCV | 180.6 | 307.6 | |
| Category 1 Germination | 17.2 | 20.9 | 0.4261 |
| Germinants per ml SCV | 40 | 88.9 | 0.1768 |
| Mean root length (mm) | 32.1 | 23.7 | 0.1481 |

The data shown above in TABLE 8 shows a statistically significant (0.10 p value cutoff) 70% increase in embryo yield with no apparent loss in germination percent, although there is some indication of difference in root length. While not wishing to be bound by theory, the difference in root size observed may be due to nutritional issues associated with the greater amount of growth. The nutritional issues can be addressed by either moving the plated embryos to a fresh growth substrate after a period of time, or by adjusting media composition to a greater concentration, and/or modifying the plating density for particular cell lines based upon their growth rate.

As shown in TABLE 8, the spread plating method of the invention resulted ill 120% yield of germinants as compared to the drop plating method, suggesting a very large improvement in culture productivity as measured by both embryo generation and germination, on a per box unit and surface area basis. This observed improvement in embryo yield allows for scale up with no limitation upon the size of the plated surface, in contrast to the previous drop method grown in petri dishes. Such scale up increases the amount of embryos formed per plated unit and decreases per unit costs by reducing the amount of manipulation required.

Although this Example describes the use of Cambro boxes as plating containers, the plating containers for the development step following plating can be any suitable plating surface, such as any box type containers, such as commercially available food preparation containers that are heat stable and have a lid that can be used.

The liquid dispersion confluent spreading method has also been successfully carried out using a plating frame disposed over a variety of non-porous sterile surfaces besides semi-solid media, such as for example, a sterile plastic lid, or a silicon sheet or a rubber mat placed into a vessel capable of retaining liquid, followed by contacting the plated embryos with development medium.

The liquid dispersion confluent spreading method has also been successfully carried out by first plating an amount of sterile dilution media sufficient to submerge a plating surface comprising a porous material disposed over a solid (non-porous) substrate. The desired volume of SCV is then added to the dilution media and gently mixed with a pipette. The floating cells are then dispersed with the optional aid of a pipette and/or gentle agitation of the first plating surface. The plating frame is then picked up and placed over a second growth substrate comprising development media and incubated as described supra.

Finally, the confluent spreading method has also been successfully used to generate embryos from various Loblolly Pine genotypes using aliquots of from 1 ml up to 12 ml SCV plated onto an entire plating frame (7"×4") placed on semi-solid development media.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of producing conifer cotyledonary somatic embryos, the method comprising:
   (a) uniformly dispersing pre-cotyledonary somatic embryos onto a porous material horizontally disposed over a non-porous surface at a density of less than 0.05 gram wet cell weight of pre-cotyledonary somatic embryos per square inch of porous material by suspending the pre-cotyledonary embryos in a volume of sterile dilution medium sufficient to submerge the surface of the porous material and dispensing the pre-cotyledonary somatic embryos in the sterile dilution medium onto the porous material;
   (b) removing the sterile dilution medium from the porous material, thereby trapping the uniformly dispersed pre-cotyledonary somatic embryos on the porous material; and
   (c) contacting the pre-cotyledonary somatic embryos trapped on the porous material with development medium for a period of time sufficient to produce conifer cotyledonary somatic embryos.

2. The method of claim 1, wherein the pre-cotyledonary somatic embryos are uniformly dispersed according to step (a) at a density of from 0.001 gram to 0.05 gram wet cell weight of pre-cotyledonary somatic embryos per square inch of porous material.

3. The method of claim 1, wherein the porous material comprises pores having an average pore diameter in the range of from 5 microns to 1200 microns.

4. The method of claim 1, wherein the porous material is non-absorbent.

5. The method of claim 3, wherein the porous material is a woven mesh.

6. The method of claim 1, wherein the porous material is attached to a support frame comprising handles.

7. The method of claim 6, wherein the sterile dilution medium is removed from the porous material according to step (b) by vertically lifting the support frame off the non-porous surface.

8. The method of claim 1, wherein the sterile dilution medium is removed from the porous material according to step (b) by reducing the sterile dilution medium to a level below the surface of the porous material.

9. The method of claim 1, wherein the development medium according to step (c) is a liquid medium.

10. The method of claim 1, wherein the development medium according to step (c) is a solid medium.

11. A method of producing conifer cotyledonary somatic embryos comprising:
    (a) culturing conifer embryogenic cells in a liquid maintenance medium to form pre-cotyledonary conifer somatic embryos;
    (b) uniformly dispersing the pre-cotyledonary somatic embryos prepared in step (a) onto a porous material horizontally disposed over a non-porous surface at a density of less than 0.05 gram wet cell weight of pre-cotyledonary somatic embryos per square inch of porous material by suspending the pre-cotyledonary embryos in a volume of sterile dilution medium sufficient to submerge the surface of the porous material and dispensing the pre-cotyledonary somatic embryos in the sterile dilution medium onto the porous material;
    (c) removing the sterile dilution medium from the porous material, thereby trapping the uniformly dispersed pre-cotyledonary somatic embryos on the porous material; and
    (d) contacting the pre-cotyledonary somatic embryos trapped on the porous material with development medium for a period of time sufficient to produce conifer cotyledonary somatic embryos.

* * * * *